US006852543B2

(12) United States Patent
Allen et al.

(10) Patent No.: US 6,852,543 B2
(45) Date of Patent: Feb. 8, 2005

(54) METHOD AND APPARATUS FOR MEASUREMENT OF SULFATE (75) Inventors: George Allen, Swampscott, MA (US); David Harrison, Haxby (GB)

(73) Assignee: President and Fellows of Harvard College, Cambridge, MA (US)

(*) Notice: Subject to any disclaimer, the term of this patent is extended or adjusted under 35 U.S.C. 154(b) by 0 days.

(21) Appl. No.: 10/611,416

(22) Filed: Jul. 1, 2003

(65) Prior Publication Data
US 2004/0082072 A1 Apr. 29, 2004

Related U.S. Application Data (63) Continuation of application No. PCT/US02/00047, filed on Jan. 2, 2002.
(60) Provisional application No. 60/259,350, filed on Jan. 2, 2001.

(51) Int. Cl.[7] .............................................. G01N 33/00
(52) U.S. Cl. ..................... 436/122; 436/102; 436/119
(58) Field of Search ................................ 436/102, 119, 436/122; 423/539, 544, 574.1

(56) References Cited

U.S. PATENT DOCUMENTS

| 3,845,309 | A | 10/1974 | Helm et al. |
| 4,432,939 | A | 2/1984 | Watanabe et al. |
| 4,942,018 | A | 7/1990 | Munk |
| 5,597,480 | A | 1/1997 | Zhou |
| 5,716,852 | A | 2/1998 | Yager et al. |
| 5,957,579 | A | 9/1999 | Kopf-Sill et al. |
| 5,983,732 | A | 11/1999 | Hering et al. |
| 6,048,498 | A | 4/2000 | Kennedy |
| 6,063,589 | A | 5/2000 | Kellogg et al. |

FOREIGN PATENT DOCUMENTS

| GB | 575444 A1 | 9/1980 |
| JP | 084359 A | 3/2000 |

OTHER PUBLICATIONS

Roberts et al. "Analysis of sulfur in deposited aerosol particles by vaporization and flame photometric detection" Atmospheric Environment (1967–1989) (1976), 10(5), 403–8, Abstract.*

Zolner et al. "Source level sulfur dioxide analysis via pulsed fluorescence" Analysis Instrumentation (Research Triangle Park, North Carolina) (1974), 12, 9–17, Abstract.*

Thermo Electron Corporation, "Advanced Atmospheric Particulate and Trace Monitoring Solutions Launched," http://www.thermo.com/com/cda/newsevents/news_detail, Aug. 5, 2004, 2 pgs.

Thermo Electron Corporation, "Model 5020 SPA, Sulfate Particulate Analyzer," http://www.thermo.com/com/cda/newsevents/news_detail, Aug. 5, 2004, 1 page.

International Preliminary Examination Report of International Application No. PCT/US02/00047, dated May 13, 2003.

Roberts et al., "Analysis of Sulfur in Deposited Aerosol Particles by Vaporization and Flame Photometric Detection", (Nov. 25, 1975), pp. 403–408.

Jaklevic, et al., "Automatic Particulate Sulfur Measurements With a Dichotomous Sampler and On–Line X–ray Fluorescence Analysis", vol. 15, No. 6, (Jun. 1981), pp. 687–690.

(List continued on next page.)

Primary Examiner—Yelena G. Gakh
(74) Attorney, Agent, or Firm—Wolf, Greenfield & Sacks, P.C.

(57) ABSTRACT

A method and apparatus for sulfate analysis in a sample are provided. A portion of the sulfate contained in the sample is converted to sulfur dioxide, and at least a portion of the sulfur dioxide can be determined. The amount of sulfur dioxide determined can be used to quantify the amount of sulfate in the sample.

39 Claims, 3 Drawing Sheets

OTHER PUBLICATIONS

Allen, et al., "A New Method for Continuous Measurement of Sulfate in the Ambient Atmosphere", (Oct. 18, 2001), pp. 1–14.

Barden, EPA Project Summary: "Analysis System for Total Sulfuric Acid in Ambient Air–Development and Preliminary Evaluation", (May 1981), pp. 1–4.

Buhr, et al., "Development of a Semi–Continuous Method for the Measurement of Nitric Acid Vapor and Particulate Nitrate and Sulfate", vol. 29, No. 19, (Mar. 24, 1995), pp. 2609–2624.

Camp, et al., "Intercomparison of Concentration Results From Fine Particle Sulfur Monitors", vol. 16, No. 5, (May 22, 1981), pp. 911–916.

Cobourn, et al., "Continuous *In Situ* Monitoring of Ambient Particulate Sulfur Using Flame Photometry and Thermal Analysis", vol. 12, (Oct. 5, 1977), pp. 89–98.

D'Ottavio, et al., "Determination of Ambient Aerosol Sulfur Using a Continuous Flame Photometric Detection System II. The Measurement of Low–Level Sulfur Concentrations Under Varying Atmospheric Conditions", vol. 15, (Mar. 31, 1980), pp. 197–203.

Garber, et al., "Determination of Ambient Aerosol and Gaseous Sulfur Using a Continuous FPD III. Design and Characterization of a Monitor for Airborne Applications", vol. 17, No. 7 (Dec. 13, 1982), pp. 1381–1385.

Hoek, et al., "Concentrations of Acidic Air Pollutants in the Netherlands", vol. 30, No. 18 (Jan. 12, 1996), pp. 3141–3150.

Huntzicker, et al., "Continuous Measurement and Speciation of Sulfuer–Containing Aerosols by Flame Photometry", vol. 12, (Aug. 26, 1977), pp. 83–88.

Kamholtz, et al., "Quantitative Analysis of Molecular Interaction in a Microfluidic Channel: The T–Sensor", *Anal. Chem.*, vol. 71, No. 23, (Dec. 1, 1999), pp. 5340–5347.

Keeler, et al., "Transported Acid Aerosols Measured in Southern Ontario", (May 21, 1990), vol. 24A, No. 12, pp. 2935–2950.

Kittelson, et al., "Total Sulfur Aerosol Concentration With an Electrostatically Pulsed Flame Photometric Detector System", vol. 12, (Sep. 7, 1977), pp. 105–111.

Lodge, "Methods of Air Sampling and Analysis Third Edition", (1988), pp. 527–533.

"Series 8400S Ambient Particulate Sulfate Monitor: Quantitative, Time–Resolved Measurement of Particulate Sulfate Contained in Ambient Fine Particulate Matter", Rupprecht & Patashnick Co., Inc. (Jul. 2001), pp. 1–4.

"Series 8400N Ambient Particulate Sulfate Monitor", (Dec. 19, 2001), pp. 1–2.

"Features Sheet Series 8400S Ambient Particulate Sulfate Monitor", (Mar. 2001), pp. 1–2.

Slanina et al., "Determination of Sulfuric Acid and Ammonium Sulfates by Means of a Computer–Controlled Thermodenuder System", *Anal. Chem.* vol. 57, No. 9, (Aug. 1985), pp. 1955–1960.

"Comments on Determination of Sulfuric Acid and Ammonium Sulfates by Means of a Computer–Controlled Thermodenuder System", *Anal. Chem* vol. 58, (1986), pp. 653–654.

"Thermo Environmental Instruments (TEI) Model 15C Gas Filter Correlation HCI Analyzer", (Jan. 2, 2002), pp. 1–15.

Lee, et al., "Aerosols: Research, Risk Assessment and Control Strategies", (May 19–25, 1985), pp. 105–120.

Suh, et al., "Field Method Comparison for the Characterization of Acid Aerosols and Gases", vol. 28, No. 18, (Mar. 29, 1994), pp. 2981–2989.

Tanner, et al., "Determination of Ambient Aerosol Sulfur Using a Continuous Flame Photometric Detection System 1. Sampling System for Aerosol Sulfate and Sulfuric Acid", vol. 14, (Jul. 19, 1979), pp. 121–127.

Weigl, et al., "Microfluidics: Microfluidic Diffusion–Based Separation and Detection", *Science*, (Aug. 28, 2000) 283 (5400):346, pp. 1–4.

International Search Report dated Jan. 24, 2003 for International Application No. PCT/US 02/00047.

Maddalone, et al., "Measurement of Sulfuric Acid Aerosol and Total Sulfate Content of Ambient Air", *Environmental Science & Technology*, (Feb., 1996) pp. 162–168.

Written Opinion dated Mar. 13, 2003 for International Application No. PCT/US 02/00047.

\* cited by examiner

METHOD AND APPARATUS FOR MEASUREMENT OF SULFATE

RELATED APPLICATIONS

This application is a continuation of International Application No. PCT/US02/00047 filed Jan. 2, 2002, which was published under PCT Article 21(2) in English, and claims priority to U.S. application Ser. No. 60/259,350, filed Jan. 2, 2001. Both applications are hereby incorporated by reference.

FIELD OF THE INVENTION

The invention relates to a method and apparatus for monitoring air quality and specifically to a method and apparatus for providing a continuous technique for monitoring particulate sulfate concentration in air samples.

BACKGROUND OF THE INVENTION

Air pollution analysis and monitoring has become increasingly sophisticated as more is learned about the health effects of the specific components of air pollution and as analytical techniques improve to provide better analyte selectivity and lower detection levels.

Aerosols are one air pollution component receiving increased scrutiny. In particular, sulfur particulates, i.e., suspended particles, in air, that consist at least partially of sulfur, are of concern. This suspended material, whether or not it contains sulfur, is referred to as "PM" (particulate matter or particulate material) and is one component of combustion related aerosols, which are believed to contribute to health problems related to air pollution. Health-related effects may be most severe during periods of high concentration of these materials (PM events) in the atmosphere. Particles containing a high proportion of sulfur may be particularly harmful, and it is believed that the smaller particles may be of greatest concern. Data show that most sulfur-containing particles of less than about 1 micron in size are produced by stationary sources, such as fossil fuel power plants, and that particles larger than about 1 to 3 microns are mechanically introduced, rather than products of combustion.

The United States Environmental Protection Agency (EPA) has set standards at two different particle size thresholds, PM 2.5 (particles less than 2.5 microns in size) and PM 10 (particles less than 10 microns in size). Of particular interest, due to the health effects, is PM 2.5, for which a direct correlation with increased morbidity has been shown. As the sulfur content of these particles may be the greatest contributor to increased morbidity, the measurement of sulfate containing particles less than 2.5 microns in size is of particular interest.

As it is believed that the prevalent form of sulfur in particulate matter is sulfate, sulfate is of primary concern and analytical results may be reported in terms of either sulfur or sulfate.

Sulfate analysis presents a number of problems to the environmental analyst, including volatility, reactivity and stability. One current method of particulate sulfate analysis includes flame photometric detection (FPD), such as described in Appel, B R, R L Tanner, D F Adams, P K Dasgupta, K T Knapp, G L Kok, W R Pierson, K D Reiszner (1989); Method 713: "Semi-Continuous Determination of Atmospheric Particulate Sulfur, Sulfuric Acid, and Ammonium Sulfates" is described in Methods of Air Sampling and Analysis, 3rd edition, J P Lodge, Jr., editor, Lewis Publishers, Inc., Chelsea, Mich. This technique is a labor intensive method that requires specialized training as well as a source of hydrogen. Other methods include automated wet collection followed by ion chromatography (IC) analysis and single particle analysis using Time of Flight coupled with Mass Spectroscopy. Of particular use to those skilled in the art would be a method capable of accurately measuring particulate sulfate without requiring extensive user training or the use of explosive gasses or expensive instrumentation. In addition, to accurately characterize a PM event, a continuous measurement would provide more useful information than does a snapshot, or batch-type, analysis.

SUMMARY OF THE INVENTION

The invention provides for a variety of methods and devices for determining the presence of, and/or the quantity of sulfate, such as particulate, or aerosol, sulfate in air quality analysis.

In one aspect, a method includes providing a sample comprising sulfate, converting at least a portion of the sulfate to sulfur dioxide and continuously determining the sulfur dioxide.

In one embodiment, a method is provided that includes passing a sample optionally in the form of a fluid, comprising sulfate over a surface, the surface comprising a transition metal and being at an elevated temperature. At least a portion of the sulfate is reduced to sulfur dioxide, and at least a portion of the sulfur dioxide is continuously determined.

In another aspect, a device is provided comprising a surface comprising a transition metal and a sulfur dioxide detector in fluid communication with the surface.

In another aspect, a method is provided that includes passing air that comprises particulate across a heated surface comprising chromium, the particulate matter comprising sulfate. At least a portion of the sulfate is reduced to sulfur dioxide, and sulfur dioxide is determined.

In another embodiment, a method of measuring particulate sulfate content in a fluid sample is provided. A fluid sample including particulate matter is provided and continuously contacted with means for reducing the sulfate to sulfur dioxide. Sulfur dioxide in the fluid sample is then detected.

In another embodiment, an apparatus comprises means for continuously converting at least 80% of any particulate sulfate in the air sample to sulfur dioxide and means for analytically determining sulfur dioxide in the air sample.

Other advantages, novel features, and objects of the invention will become apparent from the following detailed description of the invention when considered in conjunction with the accompanying drawings, which are schematic and which are not intended to be drawn to scale. For purposes of clarity, not every component is labeled in the figure, nor is every component of each embodiment of the invention shown where illustration is not necessary to allow those of ordinary skill in the art to understand the invention.

DETAILED DESCRIPTION

In one embodiment, the present invention provides a method and apparatus for continuously measuring the particulate sulfate (ammonium sulfate and/or $H_2SO_4$) content, in samples such as fluids. The apparatus may be portable and can be operated without a source of compressed gas and thus may be used in numerous locations where it may be desirable to measure sulfate, such as on rooftops, in vehicles, or in aircraft. The method may be operated in a mode that provides for continuous sulfate conversion and analysis which eliminates or diminishes the need for sample collection.

"Continuously" determining or measuring or converting means using a technique that need not be performed batchwise, but rather provides results that can be sampled at varying intervals, or constantly. For instance, a continuous method may be able to provide readings at 10 minute, one minute, ten second or one second intervals. The concentration of the analyte determined at the detector may be the molar equivalent (compensating for temperature, volume, etc.) to the concentration in the raw, ambient sample. A continuous technique is capable of providing analytical results without accumulating analyte from a sample over time. However, continuous detection methods may also be useful in detecting analyte that has been accumulated over time, for instance, by impaction.

"Determining" means collecting and/or determining the presence or amount of. When collecting, the quantity or concentration may not be important, however, "analytically determining" means either detecting the presence of, or the quantity of, one or more species.

"Sample" may include any substance that may contain a species of interest. For example, the substance may be a fluid such as a gas or liquid, a solid, or a gel.

Typically, particulate sulfur in the atmosphere exists as $SO_4$, and the method can provide for measuring the $SO_4$ content in particulate matter by, for example, continuously reducing $SO_4$ to $SO_2$ and quantitatively measuring the resulting $SO_2$ concentration. Particulate matter is non-gaseous material suspended in a gas and is also referred to as aerosol.

Particulate sulfate levels may be continuously measured down to or below a concentration of 0.25 $\mu g/m^3$, or lower. Total particulate sulfate or particulate sulfate within certain particle size ranges, e.g., PM 10 and PM 2.5 events may be continuously measured or monitored.

In one aspect, the method provides for passing a sample, such as air, over a surface, at an elevated temperature. As used herein, an elevated temperature is a temperature greater than room temperature (25° C.). The sample may be a solid, gel, liquid or a gas or a mixture of fluids or gases. In some embodiments, the fluid is a gas mixture, such as air. In some instances, oxygen does not need to be removed from the gas mixture, and the mixture may include, for example, at least 5% oxygen, 10% oxygen or about 20% oxygen. At least a portion of the sulfate that is present in the gas sample may be reduced to sulfur dioxide, and the resulting sulfur dioxide, or at least a portion of the sulfur dioxide, can be detected by a method that is capable of detecting sulfur dioxide. A number of methods or instruments can be used, such as, for example, flame photometry, mass spectroscopy, coulometry, gas chromatography with a sulfur dioxide sensitive detector, a photo ionization detector (PID), an electron captive detector (ECD), a nitrogen phosphorous detector (NPD), an atomic emission detector (AED), a post-discharge helium ionization detector (PDHID), or a pulsed fluorescence detector (PFD)). The presence or amount of sulfate in the sample can be indirectly determined by measuring the presence or amount of sulfur dioxide at the detector.

Frequently, the sulfate is present as ammonium sulfate. The sulfate may be present in particulate form, and specific size ranges of PM may be independently analyzed. For example, the group of particles tested may be total particles, those less than about 10 microns in size, those less than about 2.5 microns in size or those less than about 1 micron in size.

Particles can be screened by size using methods known to those skilled in the art. Useful results may be obtained at temperatures greater than 500° C. High efficiency results may be obtained at surface temperatures of greater than 800° C. and increased efficiencies may be obtained at temperatures greater than 900° C. or 1000° C. In some embodiments, the surface is at a temperature of about 1100° C., or greater.

In one embodiment, the sample being analyzed, such as an air sample, may be passed directly across the converter surface without a need for accumulating particles over time as may be required with some batch type or non-continuous techniques. This also means that the sulfate can be converted to sulfur dioxide without a need for a second fluid, such as nitrogen or purified air. Thus, a sample can be passed over a surface at an elevated temperature and sulfur dioxide can then be determined without a step of concentrating the target analyte.

Traditionally, the reduction of sulfate to sulfur dioxide has been difficult, particularly in the presence of air, with a substantial portion of the sulfate being reduced only to $SO_3$. The present invention, however, provides for greater than 50%, 80%, 90%, 95%, and greater than 99% conversion of $SO_4$ to $SO_2$. Continuous measurements over the range of 0.25 to 40 $\mu g/m^3$ $SO_4$ may be made. Additional ranges up to 1, 10 and 20 $\mu g/m^3$ may also be employed.

Experimental data show that temperature alone is inadequate to reduce $SO_4$ to sulfur dioxide in air. It is believed that the conversion of $SO_4$ to $SO_2$ is a result of reacting $SO_3$, which is readily formed through the reduction of $SO_4$, with a transition metal, a salt of a transition metal, or a carbide to form $SO_2$. Preferably, the metal can exist in several oxidation states, and salts of metals having three or more oxidation states may be more preferred.

One reaction mechanism that may account for the effective conversion of sulfate to sulfur dioxide is shown in Equation 1. At high temperature, sulfate may be reduced to $SO_3$ gas. It is believed that the $SO_3$ then contacts a hot surface that includes a metallic element, such as chromium and is further reduced to sulfur dioxide.

(Eq.1)

It is believed that the reduction from $SO_4$ to $SO_2$ can be facilitated by either the catalytic effect of a metal such as chromium that may be present on the surface over which the fluid sample passes or by a non-catalytic mechanism whereby $SO_3$ reacts with chromium to form $SO_2$ (Eq.2). The appearance of chromium salts downstream of the converter points to the latter mechanism. It is notable that this reduction process occurs in a highly oxidative atmosphere (air) at high temperature (for instance, greater than 500° C., 800° C., 900° C. or 1000° C.), conditions which are typically not favorable to reductive reactions. One mechanism that may account for this reduction reaction is as follows:

$SO_3$+[Cr(II) and/or Cr(III)]→$SO_2$+[Cr(IV) and/or Cr(VI)]  (Eq.2)

In one embodiment, the surface may contain transition metals such as chromium and therefore materials such as chromium carbide, chromium salts, and metals and alloys containing chromium, may be suitable surfaces for the reduction of $SO_4$ (or $SO_3$) to sulfur dioxide. Analogous compounds such as tungsten carbide may also provide good conversion efficiencies. The metallic component of these compounds may facilitate reduction of sulfate by providing a source of electrons. If chromium is used, the chromium may be chromium carbide and more preferably is present on the surface in an amount greater than about 0.05%, by weight. In one embodiment, the surface is stainless steel, such as 316 stainless steel, which has been shown to provide conversion efficiencies of greater than 90%, is able to withstand high temperatures, and is readily available in the form of tubing. Stainless steel is a chromium steel alloy typically containing greater than 10% chromium. Specifically, 316 stainless is composed of, in part, iron, carbon, chromium, nickel and molybdenum. (See ASTM A269-01). Thus, one or more of these elements, combinations of these elements, or compounds comprising these elements may provide the reduction mechanism for reducing $SO_4$ and/or $SO_3$ to sulfur dioxide. In addition, steel is conductive and may be heated through direct resistance heating, thus providing an easily heated, reactive surface. The surface may form part of a sulfate converter that may supply heat to the surface at the required temperature and may help to insulate the surface from the external environment. Alternatively, the converter may be the surface itself.

The conversion of sulfate to sulfur dioxide by one or more chromium compounds may not be a catalytic reaction, but rather a reaction in which the chromium compound participates as a reactant. Ammonium sulfate and sulfuric acid typically decompose above 250° C. and 100° C., respectively, to give sulfur trioxide ($SO_3$). It is believed that chromium trioxide (Cr(II) and Cr(III)) can then reduce $SO_3$ to give $SO_2$ and an oxidized form of chromium (Cr(IV) or Cr(VI)) or a chromium compound. A yellow film has been observed on the surface of a quartz tube (sulfate converter) at the point where it cools down to a few hundred degrees above ambient temperature. This yellow film may be chromium (VI) oxide or a dichromate salt. In addition, downstream from the converter, a yellow tint is occasionally observed, and this may also be chromium oxide or an oxidized chromium salt. Thus, the conversion may work by the oxidation of chromium or a chromium salt and the concurrent reduction of $SO_3$ to give $SO_2$. A method is provided in which sulfate may be reduced to sulfur dioxide by passing a fluid sample containing sulfate over a surface including a chromium compound, at a temperature of 500, 600, 700, 800, 900, 1000, 1100° C., or greater.

The surface may be of any shape or form that allows for adequate contact time with the gas sample in order to convert a substantial portion of the sulfate to sulfur dioxide. For example, the surface may be in the form of a chamber, filament, tube, "wool," column, grating or packing. Preferably, the volume of the converter is small enough so that a substantial portion of the gas sample is contacted with the surface during analysis and so that the residence time of the sample in the converter is short, such as, for example, less than about 10 seconds. For example, the surface may be a coiled tube having a ⅛ inch OD and being about 6 ft in length. In another embodiment, the converter may be an inert chamber containing the surface, which may be, for example, stainless steel, chromium carbide powder or oxides of iron. As the method may be operated continuously, it is preferred that the volume of the converter be sized according to the capacity of the downstream detector, to reduce the effects of deadspace. High conversion efficiency may not be required, particularly when the actual conversion efficiency is know and repeatable, and thus can be compensated for.

Figure 2:
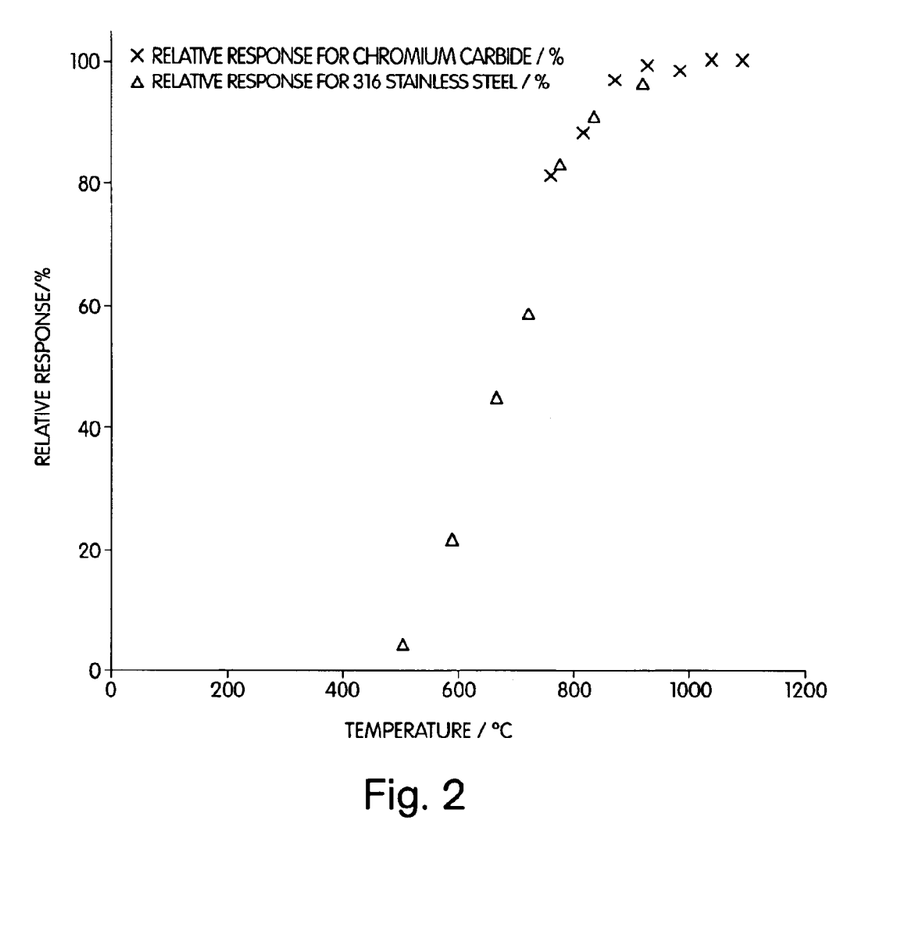
FIG. 2 provides a graphical representation of the response of two embodiments of the invention when operated at different temperatures.

At high temperatures, it is believed that chromium carbide ($Cr_3C_2$) may be formed on surfaces containing chromium, such as stainless steel tubing, from, for example, the reaction of chromium with carbon in the surface material or in the form of organic compounds in the air. Experimental data show that reaction with chromium carbide provides a conversion efficiency essentially identical to the efficiency observed with 316 stainless steel. See FIG. 2.

It is believed that other metals, particularly transition metals, may also be used to convert sulfate to sulfur dioxide. For example, other carbide compounds, such as tungsten carbide, may also provide for adequate conversion efficiency. A screening test can be used to determine which of these compounds may be appropriate. The simple test may be run, for example, by placing a small amount of a powdered compound, for example a metallic salt, in a quartz furnace and heating the furnace to a high temperature, for example, 1000° C. After the furnace has attained temperature, a gaseous sample containing a known quantity of ammonium sulfate aerosol, that is free of sulfur dioxide, can then be passed over the sample of metallic salt and upon exiting the furnace can be analyzed with a fluorescence detector to quickly determine how much, if any, of the sulfate has been converted to sulfur dioxide. Compounds screened in this manner may then be further categorized as to their appropriateness of use by including factors such as cost, availability, durability and safety. Samples may also be tested at different temperatures or under other conditions to determine applicability for different applications of the test method.

In one embodiment, the converter may comprise metals or compounds containing metals that have three or more oxidation states. In another embodiment, the metals or metal containing compounds may have four or more oxidation states. These compounds exhibiting elements having multiple oxidation states may allow for fast and efficient reduction of sulfate or $SO_3$ to sulfur dioxide.

It is believed that salts of metals exhibiting multiple valences, for example, 2, 3, 4, 5 and 6, may be the preferred group for converting $SO_4$ to sulfur dioxide at an elevated temperature. This is believed to be due to the multiple oxidation states available that allow the sulfate (or $SO_3$) to be efficiently reduced to $SO_2$. In particular, the transition metals may form compounds that can act as efficient reducing agents. For example, chromium may have valences of 1–6, tungsten exhibits valences of 6, 5, 4, 3 and 2, and molybdenum also exhibits valences of 6, 5, 4, 3 and 2. Other elements that have multiple oxidation states, and thus may be able to form compounds that reduce $SO_4$ or $SO_3$ to $SO_2$, include, for example, manganese, vanadium, titanium, technetium, tantalum and rhenium.

Experimental data also show that iron oxide (ferric or ferrous) may facilitate or participate in a reduction of sulfate to sulfur dioxide, although conversion efficiencies may not be comparable to those achieved in the presence of chromium. Thus, a surface that includes ferric oxide may provide adequate conversion results, particularly if any inefficiencies can be compensated for.

Retention time in the converter where the gas sample can contact the heated surface should be long enough to obtain the desired conversion of efficiency. A retention time of about 100 milliseconds in stainless steel tubing has been shown to provide results of >80% conversion efficiency at a temperature at or greater than 800° C.

In another embodiment, results showing a conversion efficiency of 40 or 50% were obtainable at temperatures of 500° C. or greater. Although these conversion efficiencies may not be as great as those at higher temperatures, if consistent, operation at these temperatures may provide results that are adequate to generate useful sulfate data.

Much of the sulfate in a particulate sample may be in the form of ammonium sulfate ($(NH_4)_2SO_4$). Typically, more than ½ of the total sulfate particulate content is believed to be in this form. If a portion of the sulfate that is present in the particulate matter is in a form that may be easily volatilized, it may form sulfuric acid upon volatilization, which in turn can react with surfaces such as the high-temperature surface in the converter. This may result in the non-detection of a significant portion of the sulfur contained in the particulate matter. One technique that may be used to avoid this analyte loss is to convert the sulfate to a less volatile species, prior to the sample's entry into the converter module. For example, an easily generated species or material, such as ammonia, may be added to the sample stream prior to heating. This will form a less volatile species, such as ammonium sulfate, that can be detected, and thus more easily measured.

Once the sulfate in the particulate matter has been reduced to sulfur dioxide by passing it over a heated surface, the sulfur dioxide can be determined by any number of methods sensitive to sulfur dioxide, including, for example, chemical, gravimetric, chromatographic, electrochemical and spectrometric techniques. The term "determining" includes the terms "detection" and "detecting" which refer to both a presence/absence indication as well as quantification. In a preferred embodiment, the resulting sulfur dioxide is detected by a fluorescence detector, the output signal of which may be continuously monitored and integrated to determine the sulfur dioxide concentration of the converted sample. The detector may irradiate the sample with light, preferably in the UV range, and any sulfur dioxide in the sample will fluoresce at a specific wavelength, or wavelengths, that can be detected. Detection may be enhanced with a photomultiplier or other system, physical or electronic, for amplifying the signal.

Most preferably, a pulse fluorescence detector is used for detection. A pulse fluorescence detector irradiates the sample intermittently, for example, ten times per second. Although such a detector does not provide a strictly "constant" readout, it is considered to be a continuous monitoring system for the purposes of the invention because the sample flow through the detector may be constant and a continuous output can be provided. A sample need not, but may be, concentrated, such as by impaction, in order to be determined. Data is sampled so frequently that when compared to other measurement time periods, e.g., one hour, the great number of sample points within the time period results in an essentially continuous reading. In addition, a "snapshot" analysis of the sampling stream can be taken at any chosen point in time.

Once the fluorescent intensity has been quantified, the signal may be converted to sulfur dioxide concentration. When the sulfur dioxide concentration is known, the sulfate concentration in the initial sample may be determined using a one to one molar conversion between the sulfur dioxide detected and the sulfate contained in the original sample. No concentration or dilution of the sample is necessary, so the concentration detected may be directly proportional to the concentration in the sample.

A pulsed fluorescence detector may be able to measure levels greater than 30 $\mu g/m^3$ sulfate, or less than 0.5 $\mu g/m^3$ sulfate. Results may be reported in $\mu g/m^3$ sulfate or in ppb (vol/vol) $SO_2$, with 3.93 $\mu g/m^3$ of $SO_4$ being about equivalent to 1 ppb $SO_2$ gas in air, at standard atmospheric temperature and pressure. By taking non-destructive, discreet, fixed-volume readings at atmospheric pressure, a pulse fluorescence detector can provide accurate results independent of any variation in the flow of the fluid sample through the detection cell. However, continuous sample flow through the detector is still preferred when air sample results are to be averaged over time, for example, during a "one hour averaging" procedure.

Although not necessary for continuous particulate sulfate analysis, optional pretreatment strategies may be employed to improve, for example, the scope, accuracy, precision and detection limit of the analysis. For example, $SO_2$, or other compounds, contained in the fluid sample, that might bias analytical results if allowed to remain in the sample, may be removed from the sample by a scrubber. A scrubber should remove gaseous contaminants without removing particulate matter. A scrubber may be any device that can remove these unwanted compounds without significantly affecting the concentration of the particulate matter of interest. Scrubbers include, for example, coated denuders, aluminum honeycomb gas scrubbers, activated charcoal, chromium trioxide, and PURAFIL® $KMnO_4$ canisters (Purafil Inc., Doraville, Ga.). Scrubbers are known to those skilled in the art, are readily available, and may be placed in series with the sulfate converter, preferably upstream of the converter.

In addition, a particle size discrimination technique may also be employed to limit the analysis to particles within a chosen size range. Any appropriate particle separator may be used. These techniques may include the use of, for example, an inertial impactor or cyclone inertial separator. Inertial impactors may include a polyurethane foam substrate, and preferably can operate at a flow of about 0.45 L/min. Such a device may be used to eliminate particles greater than 10 micron in size, greater than 2.5 micron in size, greater than 1 micron in size, or any other size range that provides useful results. If a higher volume flow is used, e.g. 16.7 L/min, the flow stream may be split isokinetically to arrive at the desired flow volumes. By eliminating particles within a certain size range, only the remaining particles may pass through the converter and be measured. This may help to maintain a clean system.

If used, it is preferred that both the sulfur dioxide removal and particle segregation are performed upstream of the conversion of particulate sulfate to sulfur dioxide. In addition, if pretreatment such as the addition of ammonia is employed, it is also preferred that this pretreatment occur prior to the conversion of particulate sulfate to sulfur dioxide.

As particulate sulfate, rather than total sulfur, may be of primary interest, it is often preferred that other sulfur species that may produce $SO_2$ in this process be eliminated from the sample so that these species do not contribute to the final measurement. One way of compensating for these species, rather than removing them, is to perform a baseline determination, or autozero function, which can then be subtracted from the total sulfate determination in order to determine the sulfate concentration of interest. Such a baseline determination may be performed by removing particulate matter from the gaseous sample and analyzing the sample after the particulate matter has been eliminated. A variety of techniques may be used, and one method of removing the particles from the fluid is to use a HEPA filter to exclude particulates prior to passing the gas over the heated surface. Alternatively, particles may be removed from the gas through impaction or electrostatic precipitation. A resulting measurement will reveal the contribution (positive or negative) provided by the non-particulate sources of sulfate. Such an analysis may be done intermittently, for example, at 10 minute intervals, to provide an accurate baseline determination for the measurement of ambient air containing particulate sulfate. Alternatively, such an analysis may be run in parallel to the particulate analysis so that a real-time constant baseline is available. This may be performed with separate detectors or by switching with a single detector between particle free and particle laden fluid. Accurate baseline measurement may allow for the elimination of pretreatment steps used to remove sulfur dioxide from the sample prior to analysis.

Often, an operator may wish to record a continuous analysis for a fixed time period. For instance, a one hour average reading may be taken at a specific urban location at several different times of day. In such a case, the apparatus may be operated for a period of 1 hour, with a filtered background (baseline) sample being run for 10 minutes of that 1 hour period. The background analysis may be done for a continuous 10 minute period or may be interspersed throughout the hour, for example, for 5 minute time periods at intervals of 20 or 30 minutes. Alternatively, the ten minute background analysis, which may be used to autozero the instrument, may be performed at the beginning or end of the one hour period. In this manner, any portion of the signal due to background sulfate, or due to non-sulfate compounds that may contribute to, or subtract from, the signal, may be eliminated. Preferably, background analysis takes about 3 to 5 minutes. Background levels may be monitored so that when large changes in the background level occur, more frequent background subtractions are performed. Of course, background values need not be subtracted and such background subtraction may be most useful when background levels contribute significantly, e.g. greater than 5, 10, or 50% of the total level of sulfate detected.

Figure 1:
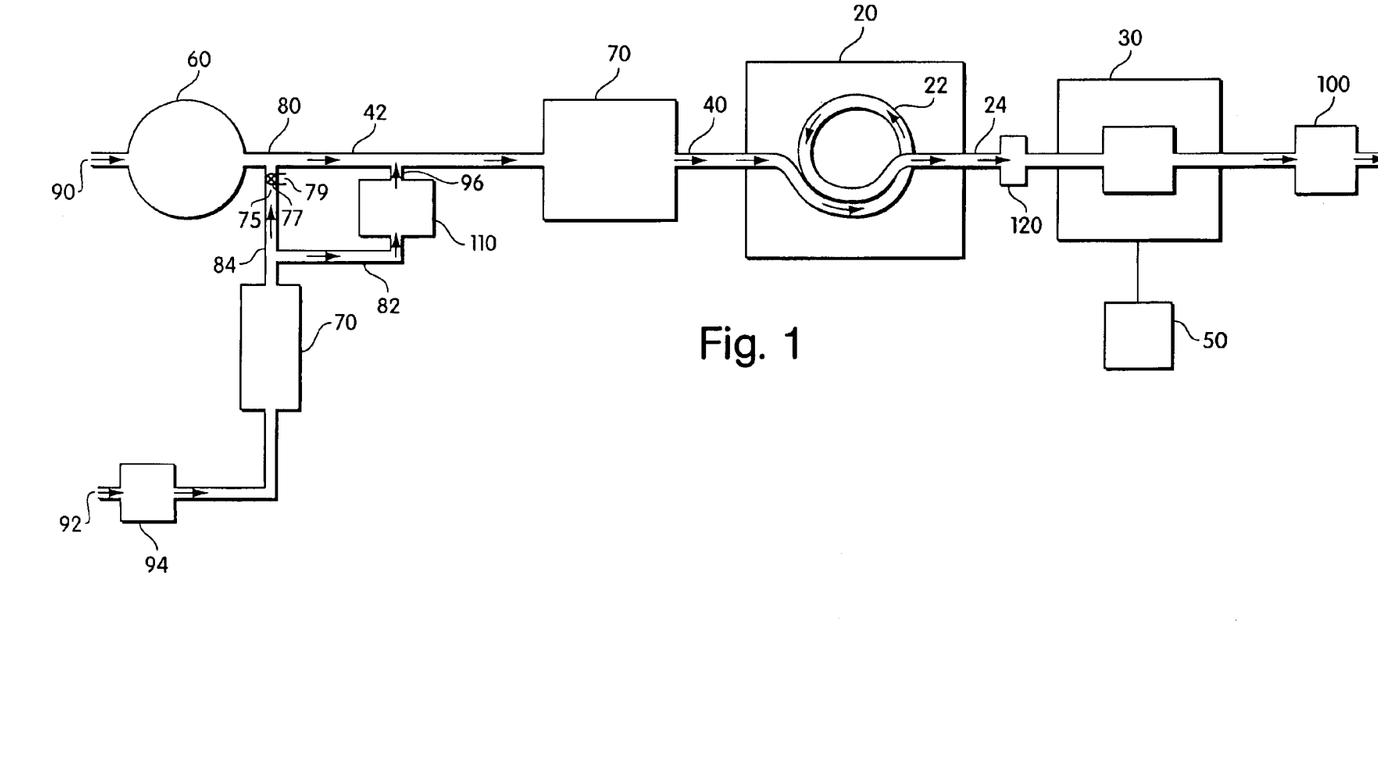
FIG. 1 provides a schematic illustration of the components of one embodiment of the invention.

FIG. 1 provides a schematic illustration of an embodiment of the invention. The device 10 may be easily operated and provides accurate results that can be used to monitor air quality in remote, rural and urban locations. It operates on standard line voltage, weighs about 30 pounds and can be operated as a mobile unit. The device may provide in situ continuous measurement results. The device has a sulfate converter 20 that includes a surface, such as a chamber, or tube 22, through which a gas, such as an air sample, passes. The conversion module operates at a temperature greater than 800° C., preferably greater than 900° C., and most preferably at about 1000° C. The tube may be heated directly or indirectly, and one such device that has been shown to operate with reasonable efficiency is the model 350 $NO_x$™ converter available from Thermo Environmental Instruments, Franklin, Mass. The model 350 converter, used to convert $NO_x$ to NO, includes a controller to maintain a constant coil temperature of 700° C. For the purposes of the present invention, the controller can be retrofitted to obtain temperatures as high as 1000° C., although at these temperatures the life of the converter may be limited to several days. The model 350 $NO_x$™ utilizes a direct resistance heating system in which a current is applied to the stainless steel coil in order to heat the coil. The conversion coil has an OD of ⅛ inch, an ID of 1/16 inch and a length of about 6 feet. It is coiled to a diameter of less than two inches. This provides a heated retention volume of about 3.6 cm³. Thus, at a flow rate of, for example, 500 cm³/min, the average retention time for a sample, at room temperature, would be about 0.43 second. At about 1000° C., however, the expansion of the gas sample (about 4x) provides for a retention time of about 0.1 second. The tubing is made of type 316 stainless steel which contains chromium that may be responsible for the conversion of sulfate to sulfur dioxide. The interior of the column can be void except for the sample being analyzed. However, it may be filled with a porous species presenting chromium in order to increase the surface area to which the sample is exposed during analysis. Similar tubes of glass or ceramic operating under similar conditions did not provide for adequate conversion unless they contained additional material.

Preferably, the converter is oriented primarily vertically so as to minimize any aerosol loss that may occur due to aerosol settling on horizontal surfaces. To minimize turbulence, it is also preferable to avoid sharp turns in the converter.

The conduits joining the different components of the device may be of any material capable of carrying a gas sample at the required flow rates. For example, the conduits may be of glass, metal or polymeric material. It is preferred that the conduit used upstream of the converter 20 is of electrically conductive material in order to avoid a static charge that may cause retention of charged aerosol particles. It is most preferred that this section of the conduit be of stainless steel. Downstream of the converter, it is preferred that the tubing be of polymeric material such as PTFE.

A filter 120 may optionally be placed between the converter 20 and the detector 30 to reduce possible contamination of the detector due to particulate material that may not be vaporized in the converter or may have been produced therein. The filter should not remove $SO_2$ from the sample stream. The filter may be composed of a variety of materials and a 2 micron pore size filter of PTFE has been shown to be effective in protecting the detector.

After exiting the conversion module at conduit 24, the sample enters a detector where the concentration of $SO_2$ may be measured. The detector may be any device capable of measuring $SO_2$ in a sample, and should have a high sensitivity for $SO_2$ and a low sensitivity for other compounds that may be present such as $CO_2$ and NO. A preferential method of detection is a fluorescence detector. Preferably, the $SO_2$ detector exhibits a high NO rejection rate. The preference for a high NO rejection rate can be diminished or eliminated by either scrubbing, such as with a charcoal filter, or adding an oxidant such as ozone, downstream of the converter and upstream of the detector. Ozone can oxidize NO to $NO_2$, thus reducing or eliminating any NO interference. The scrubber may function by removing the NO from the stream. Preferably, the treatment removes little or no $SO_2$ from the fluid stream. Such devices are known to those skilled in the art. A detector that has been shown to provide useful data is the model 43C-TLS™ sulfur dioxide detector available from Thermo Environmental Instruments, Inc., Franklin, Mass. The model 43C-TLS™ analyzer is capable of testing over a variety of concentration ranges, from 0 to 50 ppb up to 1 ppm and above with a limit of detection (LOD) of about 0.1 ppb $SO_2$. This equates to an $SO_4$ LOD of about 1.0 µg/m³ for a 10 or 15 minute sample and about 0.5 µg/m³, or better, for a 1 hour sample. The model 43C-TLS™ detector includes a microprocessor, a display panel, and a communications processor. The instrument uses a pulsed UV source lamp to provide a low detection range.

The detector 30 may communicate with a data processing system 50 that can be used to monitor and record detected data. The data may be monitored locally or remotely and raw or processed data may be transmitted using, for example, a computer network or a telephone line. The same data processing system, or an alternate one, may be used to control the parameters of operation, such as valving, temperature, flow rates, start times and stop times.

If removal of $SO_2$, or other compounds from the sample, is desired, a sulfur gas scrubber 70 may be employed upstream of the conversion module in order to eliminate $SO_2$ from the fluid stream. By using a scrubber, most or all of the $SO_2$ determined at detector 30 will be a result of particulate $SO_4$ that has been converted in conversion module 20. This may aid in reducing any positive or negative bias that may result from the conversion and/or analysis of non-target chemical species.

Another device that may be employed with the apparatus is a size exclusion device 60, such as an inertial impactor, that may be used to remove particles greater than a specific size, such as 10 micron or 2.5 micron or 1 micron. In this manner, the particulate sulfate concentrations in a variety of categories, including PM 10 and PM 2.5 events, can be determined.

To adjust for background sulfate concentration, such as that which may be contained in the gaseous phase of an atmospheric air sample, a second sample source 75 may be utilized. It is preferable that the second sample source include the same non-particulate background constituents as does sample source 90. When the detection signal produced by sample source 75 is subtracted from the signal produced by air sample 90, an accurate reading reflecting only particulate matter can be continuously obtained. Sample source 75 may be identical to that of a sample being analyzed, except that particulate matter has been removed by a particle exclusion device, for example, HEPA filter 70. Pump 94 may be used to feed a gas sample through HEPA filter 70. A cartridge-type particle filter (not shown) may be placed upstream of the pump to prolong the life of the pump and the HEPA filter. Thus, for accurate baseline determination for autozero use, the gas that is feeding inlets 90 and 92 may be of identical composition. Only after treatment with HEPA filter 70 does the composition of the two gas streams differ due to the removal of particulate species.

It may be desirable to treat the gas stream with additional materials to remove or immobilize species that may adversely affect results. Other treatments may be used to stabilize the analyte. For example, ammonia may be employed to reduce volatilization of sulfate from particulate matter. For instance, ammonia may be useful in reducing quantities of $H_2SO_4$ that otherwise may cause inaccurate results by, for example, reacting with the heated surface upon contact. Treatment agents such as ammonia may be added in a number of ways, including direct injection or through the use of an ammonia permeation tube 110. As illustrated, the permeation tube is configured so that particle-free air may be supplied to the tube from HEPA filter 70. Valving may be used to assure a steady supply of gas to the permeation tube or, alternatively, flow constrictors may be placed, for example, in conduits 82 or 84 in order to maintain a constant flow through the system. For example, if pump 94 supplies air at a rate of 0.8 L/min, the tubing may be configured so that a constant flow of about 5 or 10 mL/min is maintained through the permeation tube. The balance, a flow of about 0.7 to 0.79 L/min passes through conduit 84. If bleeder valve 79 is positioned to feed the gas from conduit 84 to tee 80, the gas will continue through conduit 42 and downstream through the device. In such a configuration, gas flow at inlet 90 is stopped, or reversed, so that the entire flow passing through conduit 42 is particle free gas. If bleeder valve 77 is alternatively positioned to bleed gas from conduit 84 to the environment through outlet 79 and not to tee 80, the flow through conduit 42 will be exclusively gas that is derived from inlet 90, i.e., a gas sample containing particulate matter. In either case, ammonia permeation tube 110 can continue to feed a gaseous mixture of ammonia through conduit 96 at a rate of about 5–10 mL/min.

If it is desirable to supply additives such as, for example, reactants, stabilizers or catalysts to the fluid stream, the additives may be introduced into the fluid stream at conduit 96. In this manner, reactants, such as ammonia, may be added to the system to stabilize sulfate species that may otherwise volatilize, or react, and become entrained on the surface of tube 22. By placing conduit 96 downstream of tee 80, sample streams entering through either inlet 90 or through conduit 75 may receive the same pre-treatment. If any bias is introduced by a pre-treatment step, this structure assures that both streams are biased equally. When desired, post-converter chemical addition can also be implemented.

In order to move a gas sample through the system, a pump or vacuum source may be employed anywhere throughout the system and is preferentially placed at the end of the fluid stream. Such a pump 100 may then be used to pull air through conversion module 20 and detector 30 at a constant rate. The pump may be integral to detector 30 or may be an independent unit. To perform background subtraction to compensate for any gaseous $SO_2$ or other sources of interference that may be present in the sample being analyzed, the ambient sample is pumped through HEPA filter 70 at a rate that exceeds the normal flow rate that results from the pull of downstream pump 100. This increased rate of flow from source 75 reverses the direction of flow at inlet 90 and thereby assures that most, or all, fluid passing into converter 20 has first passed through the HEPA filter. In this manner, flow may be alternated between inlets 90 and 92, thus alternating between sample analysis and particle-free background analysis by varying the flow through conduit 75 by operating solenoid value 77. This means that valving may not be necessary at tee 80.

WORKING EXAMPLES

Example 1

In one set of experiments, a system such as that shown in FIG. 1 was constructed. The sulfate converter had a surface of 316 stainless steel and was a resistance heated-tube converter (Model 350, Thermo Environmental Instruments, Franklin, Mass.) that is commercially available for NOx or ammonia analysis. The converter was modified by removing all extraneous valving and was connected via ¼ inch OD copper tubing to one end of an aerosol generator. The other end of the converter was connected via ¼ inch OD PTFE tubing to a trace level pulse fluorescence sulfur dioxide detector, the 43C-TLS™ detector available from Thermo Environmental Instruments, Franklin, Mass. A 5 µm pore size, 47 mm diameter, PTFE filter was placed in line between the converter and the detector to trap any particles that might damage the detector.

Ammonium sulfate particles were generated by bubbling dry, clean air through a 0.67 mM ammonium sulfate solution. Approximately 10 ppb V (corresponding to 40 µg/m3) of ammonium sulfate aerosol was generated and the amount was verified by sampling (in parallel to the test method) on a 47 mm diameter, 2 µm pore size, PTFE filter in a PTFE filter pack. Exposed filters were then analyzed by ion chromatography to determine time averaged particle generation rate. Conversion efficiency of the method was calculated as the net detector response to sulfate relative to aerosol-free air and was reported as a percentage of the sulfur dioxide concentration that would be expected if all of the sulfate present in the sample were converted to sulfur dioxide.

Close to complete conversion (>95%) was obtained at temperatures above 900° C. with decreased conversion efficiency at lower temperatures. At 900° C. the tubing was found to corrode quickly producing a black powder. At 775–800° C. corrosion was minimized, but a conversion efficiency of 80% was realized. Results over a temperature range of 505–920° C. are provided in Table 1 and graphically in FIG. 2.

The "blank response" column provides results that were achieved by testing a sample of deionized water. The column "ammonium sulfate response" was the $SO_2$ response realized when testing the ammonium sulfate aerosol as described above. The "net response" is the ammonium sulfate response minus the blank response. The "relative response" is a percentage of the response that would be expected if all of the ammonium sulfate present were detected.

TABLE 1

316 STAINLESS STEEL SURFACE

| Temperature (° C.) | Blank Response (ppbV) | Ammonium Sulfate Response (ppbV) | Net Response (ppbV) | Relative Response (%) |
|---|---|---|---|---|
| 920 | 1.10 | 10.3 | 9.20 | 96.0 |
| 835 | 0.60 | 9.3 | 8.70 | 90.8 |
| 775 | 0.55 | 8.5 | 7.95 | 83.0 |
| 720 | 0.50 | 6.1 | 5.60 | 58.4 |
| 665 | 0.40 | 4.7 | 4.30 | 44.9 |
| 590 | 0.35 | 2.4 | 2.05 | 21.4 |
| 505 | 0.30 | 0.7 | 0.40 | 4.2 |

Conversion efficiency of sulfuric acid was determined to be about 20% less than that obtained for ammonium sulfate, indicating that upstream treatment with ammonia to convert the sulfuric acid to ammonium sulfate would provide better conversion efficiency. Of course, chemicals other than ammonia known to those skilled in the art may also be used to treat any sample containing sulfuric acid.

Example 2

Figure 3:
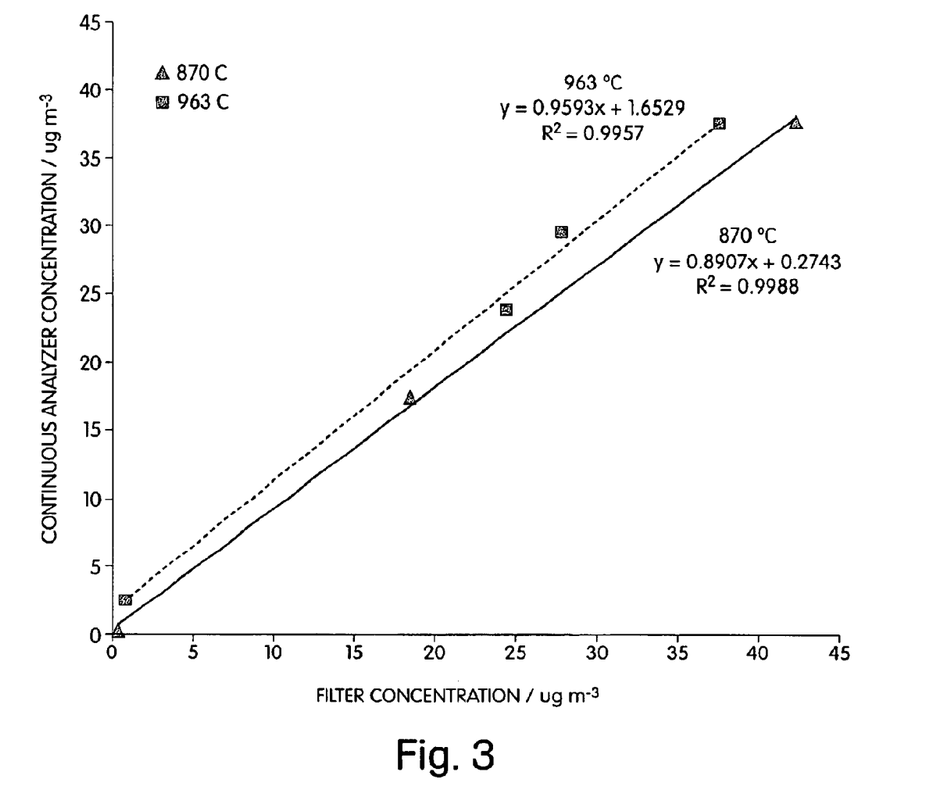
FIG. 3 provides a graphical representation of results achieved using an embodiment of the invention compared to a traditional method of particulate sulfate analysis.

A similar system to that used in Example 1 was used for another set of experiments. The converter that was used was a quartz tube furnace (Thermo Environmental Instruments, Inc., Franklin, Mass.) rather than the stainless steel tubing as was used in Example 1. To aid in determining whether or not a component in the stainless steel was responsible for the conversion of sulfate to sulfur dioxide, the furnace was operated both empty and filled with quartz wool. Ammonium sulfate particles (aerosol) were generated by bubbling dry, clean air through a 0.67 mM ammonium sulfate solution. Approximated 10 ppb V (corresponding to 40 μg/m3) of ammonium sulfate aerosol was generated and the amount was verified by sampling (in parallel to the test method) on a 47 mm diameter, 2 μm pore size, PTFE filter in a PTFE filter pack. Exposed filters were then analyzed by ion chromatography to determine time averaged particle generation rate.

The temperature of the furnace was maintained at 1100° C. Otherwise, equipment and conditions were identical to those in Example 1. Conversion of sulfate to sulfur dioxide was shown to be about 25% in both the case with quartz wool and the case without quartz wool. This poor recovery indicates that high temperature alone, or high temperature and available surface area alone, is inadequate to obtained conversion efficiencies of 50%, 80%, 90%, 95%, or more.

Example 3

In another experiment, the same furnace as that used in Example 2 was operated after placing a piece of 316 stainless steel (SS) tubing in the quartz furnace. The sample did not necessarily pass through the SS tubing, but did pass over it. Various temperatures (760–1093° C.) were employed over a range of, and at temperatures of 900° C. and greater, a conversion efficiency of about 100% was realized. 316 stainless steel contains, iron, chromium (16 to 18%), nickel (11 to 14%), molybdenum (2 to 3%), manganese (2%), silicon (0.75%), carbon (<0.08%), phosphorous (<0.04%), and sulfur (<0.03%). Thus, these results coupled with those of Example 2 illustrate that these elements, or compounds containing these elements, can cause the reduction of sulfate to sulfur dioxide at elevated temperatures.

Example 4

In another experiment, chromium carbide powder was placed in the quartz tube furnace to determine if chromium carbide might be effective at reducing sulfate to sulfur dioxide. At temperatures greater than 900° C., this substance was found to provide a conversion efficiency of about 100%, indicating that chromium carbide is an efficient converter and that a substance observed on the stainless steel in previous experiments might also be chromium carbide. Results over a temperature range of 760–1093° C. are reported in Table 2, below, and are provided graphically in FIG. 2. These results illustrate similar or improved conversion efficiencies at comparable temperatures using chromium carbide than that obtained with the stainless steel of Example 1.

The "blank response" column provides results that were achieved by testing a sample of deionized water. The column "ammonium sulfate response" was the response realized when testing the ammonium sulfate aerosol as described above. The "net response" is the ammonium sulfate response minus the blank response. The "relative response" is a percentage of the response that would be expected if all of the ammonium sulfate present were detected.

TABLE 2

CHROMIUM CARBIDE SURFACE

| Temperature (° C.) | Blank Response (ppbV) | Ammonium Sulfate Response (ppbV) | Net Response (ppbV) | Relative Response (%) |
|---|---|---|---|---|
| 760 | 2.3 | 12.3 | 9.90 | 81.1 |
| 816 | 2.4 | 13.2 | 10.75 | 88.1 |
| 871 | 2.2 | 14.1 | 11.80 | 96.7 |
| 927 | 2.5 | 14.6 | 12.10 | 99.2 |
| 982 | 2.8 | 14.8 | 12.00 | 98.4 |
| 1038 | 4.0 | 16.2 | 12.20 | 100.0 |
| 1093 | 10.5 | 22.7 | 12.20 | 100.0 |

Example 5

To illustrate the correlation between an embodiment of the present invention and a traditional method of analysis, the results realized by using the method of Example 1 (Method 1) were compared to results obtained by running a traditional filtration system followed by ion chromatography. This confirmatory method was the same as that described in Buhr et al., "Development of a Semi-Continuous Method for the Measurement of Nitric Acid Vapor and Particulate Nitrite and Sulfate," *Atmospheric Environment*, Volume 29, No. 19, pages 2609–2624, 1995, Elsevier, incorporated by reference herein. Both the Method 1 and the filtration/IC method were run in parallel using the same aerosol samples that were produced as in Example 1. To determine the effect of a temperature difference on the method of Example 1, samples were run at 870° C. and 963° C. Results for the method at 870° C. in comparison with the filter/IC method are provided in Table 3, and results from the method operated at 963° C. in comparison with the filter/IC method are provided in Table 4. The data are provided graphically in FIG. 3. The data illustrate a good correlation ($R^2$) between the traditional method and the method of Example 1 and also show a better recovery with the method of Example 1 at a temperature over 900° C. than at a temperature under 900° C.

TABLE 3

SULFATE DETERMINATION AT 870° C.

| Filter/IC ($\mu g/m^3$) | Method 1 ($\mu g/m^3$) |
|---|---|
| 0.286 | 0.102 |
| 42.390 | 37.700 |
| 18.490 | 17.500 |

TABLE 4

SULFATE DETERMINATION AT 963° C.

| Filter/IC ($\mu g/m^3$) | Method 1 ($\mu g/m^3$) |
|---|---|
| 37.68 | 37.64 |
| 27.85 | 29.60 |
| 0.83 | 2.54 |
| 24.45 | 23.95 |

Those skilled in the art would readily appreciate that all parameters listed herein are meant to be exemplary and that actual parameters would depend upon the specific systems with which the invention is used. It is, therefore, to be understood that the foregoing embodiments are presented by way of example only and that, within the scope of the appended claims and equivalents thereto, the invention may be practiced otherwise than as specifically described.

What is claimed is:

1. A method of detecting sulfate comprising:
   providing a sample comprising sulfate;
   converting at least a portion of the sulfate to sulfur dioxide; and
   continuously determining the sulfur dioxide, wherein the at least a portion of the sulfate is converted to sulfur dioxide by passing the sample over a surface comprising chromium carbide.

2. The method of claim 1 wherein the sulfur dioxide is determined via pulsed fluorescence detection.

3. The method of claim 1 wherein determining comprises quantifying the sulfur dioxide.

4. The method of claim 1 wherein at least 50% of the sulfate is converted to sulfur dioxide.

5. The method of claim 1 wherein at least 90% of the sulfate is converted to sulfur dioxide.

6. A method of detecting sulfate comprising:
   providing a sample comprising sulfate;
   converting at least a portion of the sulfate to sulfur dioxide; and
   continuously determining the sulfur dioxide, wherein the at least a portion of the sulfate is converted to sulfur dioxide by passing the sample over a surface comprising a chromium salt.

7. The method of claim 6 wherein the sulfur dioxide is determined via pulsed fluorescence detection.

8. The method of claim 6 wherein determining comprises quantifying the sulfur dioxide.

9. The method of claim 6 wherein at least 50% of the sulfate is converted to sulfur dioxide.

10. The method of claim 6 wherein at least 90% of the sulfate is converted to sulfur dioxide.

11. A method of detecting sulfate comprising:
    passing a sample comprising sulfate over a surface, the surface comprising chromium and being at an elevated temperature;
    reducing at least a portion of the sulfate to sulfur dioxide; and
    continuously determining at least a portion of the sulfur dioxide at a rate of more than one reading per second.

12. The method of claim 11 wherein the at least a portion of the sulfur dioxide is determined at a rate of about 10 times per second.

13. The method of claim 11 wherein the at least a portion of sulfur dioxide is determined via pulsed fluorescence detection.

14. The method of claim 11 wherein determining comprises quantifying the at least a portion of the sulfur dioxide.

15. The method of claim 11 wherein at least 50% of the sulfate is reduced to sulfur dioxide.

16. The method of claim 11 wherein at least 90% of the sulfate is reduced to sulfur dioxide.

17. A method of detecting sulfate comprising:
    passing a sample comprising sulfate over a surface comprising chromium carbide, the surface being at an elevated temperature;
    reducing at least a portion of the sulfate to sulfur dioxide; and
    continuously determining at least a portion of the sulfur dioxide.

18. The method of claim 17 wherein the sulfur dioxide is determined via pulsed fluorescence detection.

19. The method of claim 17 wherein determining comprises quantifying the sulfur dioxide.

20. The method of claim 17 wherein at least 50% of the sulfate is reduced to sulfur dioxide.

21. The method of claim 17 wherein at least 90% of the sulfate is reduced to sulfur dioxide.

22. A method of detecting sulfate comprising:
    passing a sample comprising sulfate over a surface comprising a metallic chromium wool, the surface being at an elevated temperature;
    reducing at least a portion of the sulfate to sulfur dioxide; and
    continuously determining at least a portion of the sulfur dioxide.

23. The method of claim 22 wherein the sulfur dioxide is determined via pulsed fluorescence detection.

24. The method of claim 22 wherein determining comprises quantifying the sulfur dioxide.

25. The method of claim 22 wherein at least 50% of the sulfate is reduced to sulfur dioxide.

26. The method of claim 22 wherein at least 90% of the sulfate is reduced to sulfur dioxide.

27. A method of detecting sulfate comprising:

passing a sample comprising particulate matter across a heated surface comprising chromium, the particulate matter comprising sulfate;

reducing at least a portion of the sulfate to sulfur dioxide; and determining sulfur dioxide via a pulse fluorescence sulfur dioxide detector.

28. The method of claim 27 wherein determining comprises quantifying the sulfur dioxide.

29. The method of claim 27 wherein at least 50% of the sulfate is reduced to sulfur dioxide.

30. The method of claim 27 wherein at least 90% of the sulfate is reduced to sulfur dioxide.

31. The method of claim 27 wherein the sulfur dioxide is determined at a rate of more than one reading per minute.

32. The method of claim 27 wherein the sulfur dioxide is determined continuously.

33. The method of claim 27 wherein the heated surface comprises stainless steel.

34. A method of detecting sulfate comprising:

passing air comprising particulate matter across a heated surface comprising chromium carbide, the particulate matter comprising sulfate;

reducing at least a portion of the sulfate to sulfur dioxide; and determining sulfur dioxide.

35. The method of claim 34 wherein determining comprises quantifying the sulfur dioxide.

36. The method of claim 34 wherein at least 50% of the sulfate is reduced to sulfur dioxide.

37. The method of claim 34 wherein at least 90% of the sulfate is reduced to sulfur dioxide.

38. The method of claim 34 wherein the sulfur dioxide is determined at a rate of more than one reading per minute.

39. The method of claim 34 wherein the sulfur dioxide is determined continuously.

* * * * *

UNITED STATES PATENT AND TRADEMARK OFFICE
CERTIFICATE OF CORRECTION

PATENT NO. : 6,852,543 B2  Page 1 of 1
APPLICATION NO. : 10/611416
DATED : February 8, 2005
INVENTOR(S) : George Allen et al.

It is certified that error appears in the above-identified patent and that said Letters Patent is hereby corrected as shown below:

Column 17, line 2, change "a sample" to --air--.

Signed and Sealed this

Fifth Day of December, 2006

JON W. DUDAS
*Director of the United States Patent and Trademark Office*